(12) United States Patent
Gutermuth et al.

(10) Patent No.: US 8,524,922 B2
(45) Date of Patent: Sep. 3, 2013

(54) PROCESS AND PLANT FOR RECOVERING SOLID REACTION PRODUCTS FROM SOLUTIONS

(75) Inventors: Thomas Gutermuth, Maintal (DE); Robert Szabo, Frankfurt am Main (DE)

(73) Assignee: Lurgi GmbH, Frankfurt am Main (DE)

( * ) Notice: Subject to any disclaimer, the term of this patent is extended or adjusted under 35 U.S.C. 154(b) by 259 days.

(21) Appl. No.: 13/062,006

(22) PCT Filed: Aug. 13, 2009

(86) PCT No.: PCT/EP2009/005883
§ 371 (c)(1),
(2), (4) Date: Mar. 3, 2011

(87) PCT Pub. No.: WO2010/028730
PCT Pub. Date: Mar. 18, 2010

(65) Prior Publication Data
US 2011/0166368 A1    Jul. 7, 2011

(30) Foreign Application Priority Data

Sep. 11, 2008   (DE) .......................... 10 2008 046 898

(51) Int. Cl.
*C07D 307/34*   (2006.01)
*C07C 51/16*    (2006.01)
(52) U.S. Cl.
USPC .......................................... 549/257; 562/408

(58) Field of Classification Search
USPC .......................... 549/258, 257; 562/407, 408
See application file for complete search history.

(56) References Cited

U.S. PATENT DOCUMENTS
3,708,532 A   1/1973   Ichikawa et al.

FOREIGN PATENT DOCUMENTS
DE    31 20 732 A1    12/1982

OTHER PUBLICATIONS

Search Report for International Application No. PCT/EP2009/005883, mailed on Nov. 5, 2009.

*Primary Examiner* — Taylor Victor Oh
(74) *Attorney, Agent, or Firm* — Leydig, Voit & Mayer, Ltd.

(57) ABSTRACT

A process for recovering solid reaction products during partial oxidation of hydrocarbons in a liquid solvent as a reaction medium by multi-stage evaporative crystallization includes determining a final temperature of the multi-stage evaporative crystallization based on a melting point of the solvent. The pressure and temperature of the solvent is reduced in steps via successive crystallization stages until the final temperature is reached. Each of the crystallization stages includes a compressor configured to perform the reducing of the pressure and to withdraw vapors formed. The vapors from the compressor of a lower expansion pressure crystallization stage are introduced into a vapor discharge conduit of a next successive higher expansion pressure crystallization stage upstream of the compressor of the higher expansion pressure crystallization stage.

20 Claims, No Drawings

PROCESS AND PLANT FOR RECOVERING SOLID REACTION PRODUCTS FROM SOLUTIONS

CROSS-REFERENCE TO PRIOR APPLICATIONS

This application is a U.S. National Phase application under 35 U.S.C. §371 of International Application No. PCT/EP2009/005883, filed on Aug. 13, 2009, and claims benefit to German Patent Application No. DE 10 2008 046 898.3, filed on Sep. 11, 2008. The International Application was published in German on Mar. 18, 2010 as WO 2010/028730 under PCT Article 21(2).

FIELD

This invention relates to a process for recovering solid reaction products during the partial oxidation of hydrocarbons in a liquid solvent as reaction medium, and to a plant for performing this process. This invention furthermore relates to the recovery of solid aromatic carboxylic acids or their acid anhydrides during the catalytic liquid-phase oxidation of alkyl-substituted aromatics, which is performed in alkyl carboxylic acids as solvent.

BACKGROUND

In the liquid-phase oxidation of alkyl-substituted aromatics in an alkyl carboxylic acid as solvent, the following borderline cases can be distinguished in principle at reaction temperature in dependence on the kind of material system with regard to the aggregation state of the target product, the aromatic carboxylic acid or its acid anhydride:
  1. The target product largely is completely crystalline at the reaction temperature.
  2. The target product still is completely dissolved in the solvent at the reaction temperature.

While in the first case a mechanical separation of the crystalline target product can be effected by simple, for instance mechanical working methods such as filtration or centrifugation without any further intermediate steps, additional process steps are required in the second case, which lead to crystallization by a decrease in temperature of the product-containing solution, before the mechanical separation of the crystals from the solution can be effected. The same is true for material systems in which the product is present in the reactor in partly dissolved and partly crystalline form.

The material systems of virtually all liquid-phase oxidation processes in use today behave such that the solution need not be cooled to initiate or promote the crystallization of the product. However, there are also carboxylic acids whose production by means of oxidation in the liquid phase is of economic interest, but which require the above-mentioned intermediate steps for a decrease in temperature with regard to the crystallization. This involves the problem that an appreciable yield of solid product requires strong cooling. Some of the alkyl carboxylic acids used as solvent also become solid in this temperature range. Therefore, care must be taken that the temperature chosen for the crystallization of the target product, which for economic reasons should be as low as possible, definitely is higher than the crystallization temperature of the solvent.

The decrease in temperature to initiate crystallization, or for the further crystallization of the product component, can for instance be effected by indirect cooling of the solution or by a step of evaporative crystallization.

When using an indirect cooling of the solution with heat exchanger surfaces, there should be a temperature difference between the cooling surface and the solution, so that heat can be withdrawn from the solution. This temperature difference should not be chosen as small as desired, since otherwise the heat exchanging surfaces become very large, which is detrimental to the economic efficiency. Therefore, there is the problem that, due to the necessity of maintaining a distance between the cooling surface temperature and the crystallization temperature of the solvent, the crystallization temperature must be chosen higher than theoretically possible for an economic removal of heat from the solution, which reduces the amount of reaction product obtained in crystalline form.

This difficulty can be overcome by applying the principle of crystallization by vacuum evaporation. In this method, the solvent usually is evaporated by an increase in temperature, whereby the solubility limit of the solid reaction product in the solvent is exceeded and the same is crystallized. DE 31 20 732 A1, for instance, describes a process for recovering sugar from suspensions of sugar crystals in juice by continuous, multi-stage evaporative condensation, in which the suspension successively is passed through a plurality of separate treatment spaces, where the juice is evaporated by supplying heat and withdrawn. However, this process involves disadvantages when thermally sensitive reaction products must be separated from solutions. Furthermore, the required high energy consumption for evaporating large amounts of solvent is disadvantageous from an economic point of view.

SUMMARY

In an embodiment, the present invention provides a process for recovering solid reaction products during partial oxidation of hydrocarbons in a liquid solvent as a reaction medium by multi-stage evaporative crystallization. A final temperature of the multi-stage evaporative crystallization is determined based on a melting point of the solvent. The pressure and temperature of the solvent is reduced in steps via successive crystallization stages until the final temperature is reached. Each of the crystallization stages includes a compressor configured to perform the reducing of the pressure and to withdraw vapors formed. The vapors from the compressor of a lower expansion pressure crystallization stage of the successive crystallization stages are introduced into a vapor discharge conduit of a next higher expansion pressure crystallization stage successive crystallization stages upstream of the compressor of the higher expansion pressure crystallization stage.

DETAILED DESCRIPTION

Therefore, the evaporative crystallization alternatively can be performed such that the reaction product is expanded into a crystallization vessel, in which a pressure exists which is smaller than the reactor pressure. The solution thereby is cooled and the temperature falls below the solubility limit of the solid reaction product in the solvent. Temperature adjustment in the crystallization vessel is effected by choosing the pressure during expansion of the solution. In a single-stage expansion, which due to the vapor pressure patterns of the components involved generally leads into the region of vacuum, in order to obtain appreciable yields of solid product in accordance with the crystallization curves of the product component, great pressure ratios between reactor pressure and expansion pressure must be overcome. In addition, the amounts of vapor obtained with a single-stage expansion are very large and require apparatuses with large dimensions.

Moreover, the apparatuses must be designed for vacuum conditions, which involves further economic disadvantages. This requires an economically acceptable and technically simple solution.

Therefore, it is an aspect of the invention to avoid the above-mentioned disadvantages and provide a more economic process for recovering solid reaction products from solutions.

In an embodiment of the present invention, the evaporative crystallization is performed as a multi-stage vacuum evaporation, wherein the pressure and the temperature in successive crystallization vessels are lowered step by step. Each crystallization stage is equipped with its own compressor for decreasing the pressure and for withdrawing the vapors formed. By guiding the vapors from the compressor of a crystallization stage of lower expansion pressure into the vapor discharge conduit of the expansion stage with the next higher expansion pressure before its compressor, the vapor volume flow obtained is minimized. The final temperature of the multi-stage evaporative crystallization is determined by the melting point of the solvent.

In accordance with an embodiment of the invention, the crystallization by vacuum evaporation is performed in several steps. From the reactor operating at excess pressure (pressure range 200-1200 kPa, preferably 300-700 kPa), the reaction solution containing the reaction product is introduced into a first crystallization vessel, which contains a stirrer for homogenization. Here, expansion is effected to a pressure slightly above the pressure existing in the waste gas system of the production process. There is obtained a temperature level corresponding to the pressure, which is lower as compared to the reactor temperature, and a first amount of solid reaction product is crystallized. During expansion, a first vapor stream is obtained, which is withdrawn and introduced into a condenser, where most of the vapors settle down. The non-condensed part of the first vapor stream at the outlet of the condenser is introduced into the waste gas system of the plant. This is possible when the expansion pressure of the first stage of vacuum crystallization is chosen as described above.

The suspension of reaction solution and first amount of solid reaction product is conveyed into a second crystallization vessel and expanded there to a lower pressure level, whereby a lower crystallization temperature is obtained. This results in a further crystallization and the formation of a second vapor stream. The same is withdrawn by means of a compressor and compressed to a pressure level which corresponds to the first crystallization stage. The compressed second vapor stream is added to the first vapor stream before the compressor of the first crystallization stage. The vapors thus obtained likewise are supplied to the above-mentioned condenser and deposited there.

This type of process control with progressive expansion of the product solution to lower and lower pressure levels is continued successively, until the pressure level in the last stage specifies that temperature which still is admissible for product crystallization in consideration of an approach to the crystallization temperature of the solvent. The vapors obtained in this stage likewise are withdrawn with a compressor, compressed to the pressure level of the preceding stage, and the vapors are supplied to the vapor discharge conduit of the preceding stage.

To avoid the condensation of the vapors at the dew point in the suction draught of the compressor or in the pipe conduits behind the same, an embodiment of the present invention provides heat to the vapors from the last crystallization stage beyond the dew point by means of a superheater. Fitting a further, several or all vapor discharge conduits of the preceding crystallization stages may also be expedient in other aspects of the invention. Utilizing the fact that each compressor stage causes further heating of the vapor stream, the outlet temperature of the superheater is chosen such that a condensation of vapors up to the first crystallization stage is safely avoided. On the other hand, the temperature of superheating should not be chosen unnecessarily high for energy reasons, as the vapors are recondensed in a further process stage, in order to be recirculated to the process in liquid form. Avoiding the condensation of the vapors in the compressors is advantageous for using less valuable materials such as stainless steel instead of titanium.

The suspension leaving the last crystallization vessel then is supplied to a separator, which performs a separation into a homogeneous solution and a thickened suspension. For this purpose, mechanical methods such as filtration or centrifugation can for instance be used. Both streams subsequently are supplied to further processing, from which the pure, solid reaction product and the solvent containing small residual amounts of reaction product are obtained as end product. To compensate losses, said solvent is replenished with fresh solvent and recirculated into the process.

For the technical design of this system, in an embodiment, the mass flow rates of crystalline product are obtained by precalculation using the crystallization curve of the target product in the solvent. The influence of further components present in the reaction solution, e.g. intermediate or by-products of the reaction, on the course of the crystallization curve are also considered.

The product solution is kept in the first and succeeding crystallization vessels with a certain residence time, in order to achieve a rather complete crystallization. This should account for kinetic effects during crystallization, such as the formation of supersaturated solutions. Alternatively or in addition, small amounts of the reaction product can be introduced into the crystallization vessels as seed crystals, in order to promote the crystallization of the reaction product.

In an embodiment, the present invention provides a plant for recovering solid reaction products during the partial oxidation of hydrocarbons in a liquid solvent as reaction medium, which is suitable for performing the process described above. The plant comprises the reactor for performing the partial oxidation, the series-connected crystallization vessels and one compressor per crystallization stage, and a condenser. Each crystallization vessel is equipped with a stirrer for homogenization. The plant furthermore comprises a separator for separation into a homogeneous solution and a thickened suspension of the reaction product in the solvent.

As an example, reference is made to the production of phthalic anhydride with acetic acid as solvent. During oxidation of o-xylene as feedstock, phthalic acid and phthalic anhydride are obtained as products in the liquid-phase reactor. Therefore, not only the binary crystallization curves of phthalic acid in acetic acid or phthalic anhydride in acetic acid are used, but also those of the ternary system phthalic acid/phthalic anhydride/in acetic acid. By using the process of the invention, phthalic acid and phthalic anhydride are obtained as pure solid products. The acetic acid obtained as byproduct is recirculated into the reactor as solvent.

Another example is the recovery of solid terephthalic acid from the reaction product of the oxidation of p-xylene by using the process according to an embodiment the present invention.

While the invention has been described with reference to particular embodiments thereof, it will be understood by those having ordinary skill the art that various changes may be made therein without departing from the scope and spirit of the invention. Further, the present invention is not limited to the embodiments described herein; reference should be had to the appended claims.

The invention claimed is:

1. A process for recovering solid reaction products during partial oxidation of hydrocarbons in a liquid solvent as a reaction medium by multi-stage evaporative crystallization, the process comprising:
reducing a pressure and a temperature of the solvent in steps via successive crystallization stages until a final temperature is reached, the final temperature of the multi-stage evaporative crystallization being based on a melting point of the solvent, wherein each of the crystallization stages includes a respective compressor configured to perform the reducing of the pressure and to withdraw vapors formed; and
introducing the vapors from the compressor of a lower expansion pressure crystallization stage of the successive crystallization stages into a vapor discharge conduit of a next higher expansion pressure crystallization stage of the successive crystallization stages.

2. The process according to claim 1, wherein the reaction products are formed during the partial oxidation of a dialkyl aromatic and include at least one of an aromatic dicarboxylic acid and an aromatic dicarboxylic acid anhydride, corresponding to the dialkyl aromatic.

3. The process according to claim 2, wherein the dialkyl aromatic is o-xylene and the reaction products include at least one of a phthalic acid and a phthalic anhydride.

4. The process according to claim 2, wherein the dialkyl aromatic is p-xylene and the reaction products include terephthalic acid.

5. The process according to claim 1, wherein the solvent includes an alkyl carboxylic acid.

6. The process according to claim 5, wherein the alkyl carboxylic acid is acetic acid.

7. The process according to claim 1, wherein each of the crystallization stages includes a stirrer for homogenization.

8. The process according claim 1, further comprising:
obtaining the reaction products by mechanical separation after the solvent passes through a last one of the successive crystallization stages.

9. The process according to claim 8, wherein the mechanical separation is performed using at least one of filtration and centrifugation.

10. The process according to claim 2, wherein the reaction products comprise an aromatic dicarboxylic acid.

11. The process according to claim 2, wherein the reaction products comprise an aromatic dicarboxylic acid anhydride.

12. The process according to claim 2, wherein the reaction products comprise an aromatic dicarboxylic acid and an aromatic dicarboxylic acid anhydride.

13. The process according to claim 2, wherein the reaction products comprise a phthalic acid.

14. The process according to claim 2, wherein the reaction products comprise a phthalic anhydride.

15. The process according to claim 2, wherein the reaction products comprise a phthalic acid and a phthalic anhydride.

16. The process according to claim 1, further comprising:
heating the vapors from the last crystallization stage beyond a dew point of the vapors.

17. The process according to claim 8, wherein the mechanical separation is performed using filtration.

18. The process according to claim 8, wherein the mechanical separation is performed using centrifugation.

19. The process according to claim 8, wherein the mechanical separation is performed using filtration and centrifugation.

20. The process according to claim 1, where the vapors are introduced upstream of the compressor of the higher expansion pressure crystallization stage.

* * * * *